March 21, 1961 S. C. JOHNSTON Plant Pat. 2,037
ROSE PLANT
Filed June 23, 1960
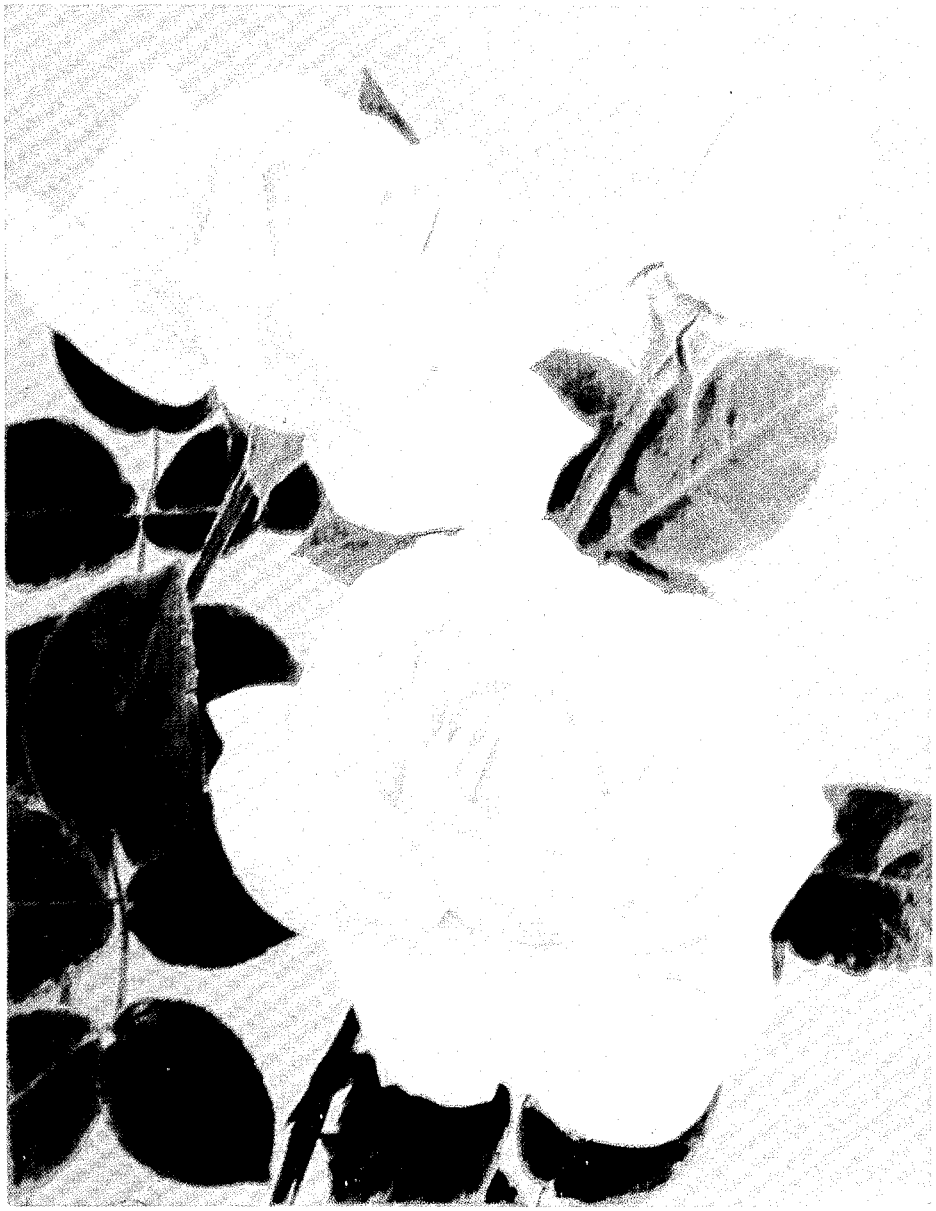
Inventor.
Stanley C. Johnston
By: Robbins & Cobb
Attorneys.

United States Patent Office

Plant Pat. 2,037
Patented Mar. 21, 1961

2,037

ROSE PLANT

Stanley C. Johnston, Wheaton, Ill., assignor to The Conard-Pyle Company, West Grove, Pa., a corporation of Pennsylvania Filed June 23, 1960, Ser. No. 38,405

1 Claim. (Cl. 47—61)

The present invention relates to a new and distinct variety of rose plant of the hybrid tea class, which was discovered by me as a cultivated bud sport of the variety "Peace" (Plant Patent No. 591).

This new rose variety was discovered by me amongst a bed of "Peace" roses that were being grown in the gardens at my residence near Wheaton, Illinois. My attention was attracted to one plant in the bed of "Peace" roses aforesaid by virtue of the fact that it bore flowers of a distinctly pink general coloration, with the base of the flower petals showing a Canary Yellow color, in contrast to the normal open flowers of "Peace" which have a general color effect of Martius Yellow color.

Upon close examination of this plant, I found that it had sported, and I thereupon took steps to preserve the sport, keep it under observation, and later asexually reproduce the same. My continued observations of original plant and the asexual reproductions thereof, as performed on my behalf by my assignee through the process of budding, at West Grove, Pennsylvania, fully confirmed the new flower characteristics of the sport and conclusively established that these characteristics come true to form and are transmissible through succeeding propagations.

Other than the specific difference in the flower color as noted in the foregoing, the new sport is substantially identical to the parent variety "Peace" and, accordingly, it is unnecessary to completely describe the new sport, since it otherwise would be substantially the same as the description appearing in Plant Patent No. 591, granted June 15, 1943, to which reference may be readily had.

There are two other sports of the variety "Peace" with which I am familiar and which bear flowers of a color somewhat similar to that of my own new sport, but the flower color of my new variety is distinctly different from that of these former sports, as well as from that of any other variety of which I am aware. Of the two previous sports referred to above, the variety which is the subject of Plant Patent No. 1,282 differs considerably in the pink coloration of its flowers, but the primary distinctive difference lies in the fact that the petals of the flowers of this patented variety have a white edging, of which there is no trace whatsoever in my new variety.

In comparison with the other prior sport referred to above, which is the subject of Plant Patent No. 1,750, the flowers of my new variety are a number of shades darker in the pink color, with the color at times reaching Spirea Red. Also, there is a more definite yellow area in the basal half of the flower petals of my new variety and as a whole, the flowers of my new variety are definitely much more highly colored.

I am also familiar with another patented variety which bears flowers of a color somewhat similar to those of my new variety. In this connection, I have reference to the variety known as "Love Song" which is the subject of Plant Patent No. 1,360. This variety is a seedling of "Peace." My new variety differs considerably therefrom in the placement of colors on the flower petals, as evidenced by the fact that the flower petals of my new variety are essentially pink, with a yellow base, whereas those of "Love Song" are generally yellow on the outside and Rose Neyron on the inside. The general color effects of the open flower, however, are more nearly similar, with the flowers of both varieties being pink in effect, with a yellow base. There are also very wide differences in the vigor and habit of my new variety as compared with those of "Love Song." My own variety is very much stronger and taller growing, with the habit of growth substantially the same as that of the parent variety "Peace," while the vigor and habit of "Love Song" fall well below those of my new variety.

It should be particularly noted that the general color effect of the flowers of my new variety is essentially a medium pink with yellow at the base, in both the bud and open flower stages, said pink color varying between Phlox Pink and Spirea Red, as compared with the British Horticultural Color Chart, and the base of the petals showing a distinct Canary Yellow color. While the flowers of the parent variety "Peace" are essentially yellow in both the bud and open flower stages, they are often marked or blotched with Rose Pink, and the fully open flowers usually bear a minimum of Rose Pink color.

The accompanying drawing shows typical specimens of the flowers and foliage of my new variety in different stages of development and as depicted in color as nearly true as it is reasonably possible to make the same in a color illustration of this character.

For convenience, the following is given as a detailed description of the flowers of my new rose variety from which the distinctions over its parent, and all other varieties, will be apparent, with color nomenclature in accordance with the Horticultural Color Chart of the Royal Horticultural Society:

*Flower*

Locality where grown and observed: West Grove, Pennsylvania.

Flowers borne: Usually singly to stem; on strong stems of medium length.

Quantity of bloom: Free, outdoors.

Continuity: Continuous.

Fragrance: Slight. Nature—tea.

Bud:

*Peduncle.*—Medium length; medium caliper; erect; stiff; medium roughness; medium number of hairs having the color of Pod Green, Plate 061. Color—Lettuce Green, Plate 861.

*Before calyx breaks.*—Size—large. Form—medium length; pointed; ovoid; with a conspicuous neck; with foliaceous appendages on the surface of the bud; with bristle-like foliaceous parts extending beyond the tip of the bud equal to ¼ or more of its length.

*As calyx breaks.*—Color—Rose Opal, Plate 022.

*As first petal opens.*—Size—large. Form—medium length; ovoid. Color: outside—Spinel Red, Plate 0023, grading to Rhodonite Red, Plate 0022, then to Delft Rose, Plate 020/1, with base of petal Canary Yellow, Plate 2/2; inside—Crimson, Plate 22/1, with basal quarter of petal Canary Yellow, Plate 2.

*Opening.*—Opens up well.

Bloom:

*Size (when fully open).*—Large; from 5 inches to 5¾ inches.

*Petalage.*—Very double; from 50 to 60 petals; arranged regularly.

*Form.*—Cupped and high-centered at first, becoming cupped; petals at first being tightly rolled inward, but later becoming loosely rolled outward at maturity.

Petals:

*Texture.*—Leathery; with both inside and outside satiny.

*Shape.*—Outer petals—roundly obovate; scalloped; with one notch. Intermediate petals—round-obovate; scalloped; with one notch. Inner petals—obovate.

This description of a newly-opened flower was made from a rose grown in a greenhouse in the month of August at London Grove, Pennsylvania:

*Color.*—Outer petal: outside surface—Phlox Pink, Plate 625/2 at margin of petal, grading to Phlox Pink, Plate 625/3, with base of petal Mimosa Yellow, Plate 602/2; inside surface—Phlox Pink, Plate 625/1, grading to Phlox Pink, Plate 625/2, with base of petal Canary Yellow, Plate 2/2. Intermediate petal: outside surface—between Phlox Pink, Plate 625/2 and Phlox Pink, Plate 625/3, with base of petal Mimosa Yellow, Plate 602/3; inside surface—Spirea Red, Plate 025/2, with base of petal Canary Yellow, Plate 2/2. Inner petal: outside surface—Mimosa Yellow, Plate 602/1, washed and striped with Phlox Pink, Plate 625/2, and heavily bordered with between Phlox Pink, Plate 625/2 and Phlox Pink, Plate 625/3; inside surface—Spirea Red, Plate 025/2, forming broad margin to the petal and bordering Naples Yellow, Plate 403/2, and lined and washed with Spirea Red, Plate 025/2, with base of petal Canary Yellow, Plate 2/2.

This description was made from a rose that was open for three days in a greenhouse in the month of August at London Grove, Pennsylvania:

*Color.*—Outer petal: outside surface—Phlox Pink, Plate 625/3, bodering Amaranth Rose, Plate 530/2, grading to Canary Yellow, Plate 2/3 over basal half of petal, and then to Canary Yellow, Plate 2/2 at base; inside surface—upper half of petal Phlox Pink, Plate 625/2, grading to Naples Yellow, Plate 403/3, with base of petal Canary Yellow, Plate 2/2. Inner petal: outside surface—

Phlox Pink, Plate 625/3, grading to Canary Yellow, Plate 2/3, washed with Phlox Pink, Plate 625/3, with base of petal Canary Yellow, Plate 2/2; inside surface—between Phlox Pink, Plate 625/2 and Phlox Pink, Plate 625/3, grading to Naples Yellow, Plate 403/3, lined with Phlox Pink, Plate 625/3, with base of petal Canary Yellow Plate 2/2.

*General color effect.*—Newly opened flower—Phlox Pink, Plate 625/2, with base of petals showing Mimosa Yellow, Plate 602/1. 3 days open—Phlox Pink, Plate 625/2, with base of petals Canary Yellow, Plate 2/3.

*Behavior.*—Drop off cleanly; in dull cloudy weather the colors are tinted lighter.

*Flower longevity.*—Cut roses grown in a greenhouse and kept at living room temperatures—3 days in August.

*Reproductive organs*

Stamens: Many; arranged irregularly about pistils.

Filaments: Medium length; most with anthers. Color—Phlox Pink, Plate 625/2.

Anthers: Open at various times; medium size; occasionally an anther fused with a petaloid. Color—Canary Yellow, Plate 2.

Pollen: Abundant. Color—Lemon Yellow, Plate 4.

Pistils: Many.

Styles: Uneven; medium length; thin; bunched.

Stigma: Color—Aureolin, Plate 3/2.

Ovaries: All enclosed in receptacle.

Hips: None observed.

Sepals: Permanent; moderately long; spear-shaped.

Seeds: None observed.

I claim:

A new and distinct variety of rose plant of the hybrid tea class, substantially as herein shown and described, characterized particularly as to novelty by being generally similar to its parent variety "Peace" (Plant Patent No. 591), but being distinguished therefrom by the Phlox Pink to Spiera Red general color tonality of its flowers, with the base of the flower petals being Canary Yellow in general color tonality.

No references cited.